United States Patent
Yoshimasa et al.

(10) Patent No.: US 7,335,810 B2
(45) Date of Patent: Feb. 26, 2008

(54) ABSORBENT ARTICLE HAVING EXTENDED CUSHION LAYER WITH CORRUGATED TOPSHEET

(75) Inventors: Wataru Yoshimasa, Kagawa (JP); Kazuya Nishitani, Kagawa (JP)

(73) Assignee: Uni-Charm Corporation, Kawanoe-Shi Ehime (JP)

( * ) Notice: Subject to any disclaimer, the term of this patent is extended or adjusted under 35 U.S.C. 154(b) by 423 days.

(21) Appl. No.: 10/194,133

(22) Filed: Jul. 11, 2002

(65) Prior Publication Data

US 2003/0088222 A1    May 8, 2003

(30) Foreign Application Priority Data

Jul. 12, 2001   (JP)   ............... 2001-212899

(51) Int. Cl.
A61F 13/533    (2006.01)
A61F 13/511    (2006.01)

(52) U.S. Cl. ............... 604/380; 604/385.101

(58) Field of Classification Search ........... 604/385.23, 604/367, 385.01, 358, 378–380, 385.101; 602/56
See application file for complete search history.

(56) References Cited

U.S. PATENT DOCUMENTS

| | | | |
|---|---|---|---|
| 3,881,490 A * | 5/1975 | Whitehead et al. ......... 604/366 |
| 4,041,951 A * | 8/1977 | Sanford ..................... 604/375 |
| 4,324,246 A * | 4/1982 | Mullane et al. ............. 604/366 |
| 4,895,568 A * | 1/1990 | Enloe .................... 604/385.27 |
| 5,308,346 A | 5/1994 | Sneller et al. |
| 5,439,458 A | 8/1995 | Noel et al. |
| 5,591,149 A | 1/1997 | Cree et al. |
| 5,833,677 A * | 11/1998 | Sauer ........................ 604/369 |
| 6,210,385 B1 * | 4/2001 | Mizutani ................ 604/385.01 |
| 6,432,094 B1 * | 8/2002 | Fujioka et al. ......... 604/385.01 |
| 6,500,159 B1 * | 12/2002 | Carvalho ................ 604/385.01 |
| 6,632,205 B1 * | 10/2003 | Sauer ..................... 604/385.01 |
| 2002/0010449 A1 * | 1/2002 | Mizutani ..................... 604/380 |

FOREIGN PATENT DOCUMENTS

| | | |
|---|---|---|
| EP | 0 345 664 A1 | 12/1989 |
| EP | 0 958 802 A2 | 11/1999 |
| EP | 0 998 893 A2 | 5/2000 |
| EP | 1 016 393 A1 | 7/2000 |
| EP | 1 097 685 A2 | 5/2001 |
| JP | 02-144059 | 6/1990 |
| JP | 2784016 | 6/1990 |
| JP | 2000-271170 | 10/2000 |
| JP | 2001-008971 | 1/2001 |
| JP | 2001-095843 | 4/2001 |
| WO | WO 99/17695 A1 | 4/1999 |

OTHER PUBLICATIONS

Austrian Patent Office Search Report for SG 200204173-9 mailed Jan. 20, 2006.
Japanese Office Action mailed Dec. 5, 2006 issued for corresponding Japanese Patent Application No. 2001-212899.

* cited by examiner

Primary Examiner—Karin Reichle
Assistant Examiner—Laura C Hill
(74) Attorney, Agent, or Firm—Darby & Darby

(57) ABSTRACT

Disclosed is an absorbent article including: a liquid-permeable topsheet; a backsheet; an absorbent storage layer between the topsheet and the backsheet; and a cushion layer between the topsheet and the absorbent storage layer. When a tensile force of 490 mN per 25 mm width is applied to the topsheet in a transverse direction crossing the cushion layer, an extension is at least 30%. When the absorbent article is pressed from above in a region having the cushion layer, an initial thickness T0 of the pressed region of the absorbent article for a pressure of 49 Pa is at least 10 mm, a compressive hardness (LC value) is 0.5 to 0.65, and a compressive recovery (RC value) is at least 35%.

14 Claims, 5 Drawing Sheets

ABSORBENT ARTICLE HAVING EXTENDED CUSHION LAYER WITH CORRUGATED TOPSHEET

CROSS-REFERENCE TO RELATED APPLICATIONS

This application claims priority under 35 U.S.C. §119 based on Japanese Patent Apllication No. 2001-212899, filed on Jul. 12, 2001.

BACKGROUND OF THE INVENTION

1. Field of the Invention

The present invention relates to an absorbent article such as sanitary napkin, urine absorbent pad, auxiliary absorbent pad for diaper or the like, more particularly to an absorbent article which is superior in fit to the wearer's body and highly effective in preventing leakage of bodily waste toward the buttocks.

2. Description of the Related Art

If the liquid-receiving region of the absorbent article is stiff, the liquid-receiving region hardly fits on the wearer's skin, causing a clearance between the absorbent article and the wearer's skin. Therefore, the bodily waste sometimes leaks from the clearance. In order to prevent this, there have been developed absorbent articles having a cushion layer between a topsheet and an absorbent storage layer to improve the contact between the absorbent article and the wearer's skin.

For example, Patent Gazette of Japanese Patent No. 2784016 discloses an absorbent article having a cushion layer in its transversely central portion close to the rear end. In the absorbent article disclosed in the above-mentioned Patent Gazette, the cushion layer is so flexible that the region having the cushion layer can fit into the gluteal fold of the wearer, thereby preventing discharged body fluid from flowing down the gluteal fold and leaking from the rear end of the absorbent article.

However, since the topsheet of the absorbent article disclosed in the above-mentioned Patent Gazette is formed of a polyester thermal-bonded nonwoven fabric in which fibers are bonded to each other, the topsheet is less extensible. Therefore, when the topsheet is pressed from above, the topsheet resists it, so that the compressive force may not act on the cushion layer. Accordingly, the flexibility of the cushion layer cannot be fully exploited, so that the absorbent article can hardly fit on the wearer's skin, especially the uneven portions such as gluteal fold. As a result, the leakage of discharged body fluid from the rear end of the absorbent article cannot be effectively prevented.

In addition, since the topsheet formed of the polyester thermal-bonded nonwoven fabric is less extensible, it gives a stiff feel to the wearer's skin. This can never provide a satisfactory feel upon wearing.

SUMMARY OF THE INVENTION

The present invention has been worked out in view of the shortcoming in the prior art set forth above. It is therefore an object of the present invention to provide an absorbent article in which a liquid-receiving surface can readily fit on uneven portions of the wearer's buttocks to improve the effect of preventing leakage of bodily waste as well as can provide a soft contact feel to the wearer's skin.

According to the present invention, there is provided an absorbent article comprising:
a liquid-permeable topsheet;
a backsheet;
an absorbent storage layer between the topsheet and the backsheet; and
a cushion layer between the topsheet and the absorbent storage layer, wherein
when a tensile force of 490 mN per 25 mm width is applied to the topsheet in a transverse direction crossing the cushion layer, an extension is at least 30%, and
when the absorbent article is pressed from above in a region having the cushion layer, an initial thickness T0 of the pressed region of the absorbent article for a pressure of 49 Pa is at least 10 mm, a compressive hardness (LC value) is 0.5 to 0.65, and a compressive recovery (RC value) is at least 35%.

In the absorbent article of the present invention, since the topsheet is extensible in the direction crossing the cushion layer, the initial thickness T0 of the region having the cushion layer can be made large, and the compressive hardness (LC value) and the compressive recovery (RC value) can be set within the above-mentioned ranges facilitating conformity to the unevenness of the wearer's body. Accordingly, the topsheet can readily come into close contact with the wearer's body, thereby preventing a bodily waste from leaking out of the absorbent article.

Preferably, when Tm represents a thickness of the pressed region of the absorbent article for a pressure of 4,900 Pa, a difference between the initial thickness T0 and the thickness Tm is at least 3 mm. In this case, the region having the cushion layer can readily conform to the unevenness of the wearer's body.

Preferably, when the cushion layer alone is pressed from above, an initial thickness T0' of the pressed region of the cushion layer for a pressure of 49 Pa is at least 3 mm, a thickness Tm' of the pressed region of the cushion layer for a pressure of 4,900 Pa is at most 1.5 mm, a compressive hardness (LC value) is at least 0.35, and a compressive recovery (RC value) is at least 30%. With the properties of the cushion layer along being set within the above-mentioned ranges, even if the absorbent storage layer is formed of a relatively hard material, the region having the cushion layer can provide an excellent contact feel to the wearer, resulting in superior feel upon wearing.

Preferably, the topsheet has a corrugated cross-sectional shape, of which hills and valleys extend in a longitudinal direction of the absorbent article. This facilitates extension of the topsheet in the direction crossing the cushion layer, so that the region having the cushion layer can be flexibly deformed when applied a pressure from the wearer's body.

Preferably, the absorbent article has a raised region in a region having the absorbent storage layer, the raised region is surrounded by a compressed groove formed by compressing the absorbent storage layer and elongated in a longitudinal direction of the absorbent article, and the cushion layer is provided in a rear region of the raised region. In such construction, since the region having the cushion layer is raised from the surface of the absorbent article and the cushion layer is positioned in the rear region, the region having the cushion layer can readily fit into the gluteal fold, preventing the leakage of bodily waste from the rear end of the absorbent article.

In this case, it is also preferred that a Gurley stiffness at a region having the compressed groove is 4.9 to 34.3 mN, a Gurley stiffness at the region having the cushion layer is 1.96 to 14.7 mN, and the Gurley stiffness at the region having the compressed groove is larger than the Gurley stiffness at the region having the cushion layer. If the region having the compressed groove has such stiffness, the shape of the raised region can be easily maintained.

Preferably, the absorbent article further comprises a pair of leakage preventing portions extending in a longitudinal direction of the absorbent article and positioned at transversely opposite sides of a region having the cushion layer, the leakage preventing portions having elastic members for exhibiting an elastic contractive force in the longitudinal direction, wherein a portion of each leakage preventing portion to be elastically contracted by the elastic member has a front end ahead of a front end of the cushion layer and has a rear end ahead of a rear end of the cushion layer. With such construction, excessive deformation of the region having the cushion layer due to the elastic contractive forces acting on the leakage preventing portions can be prevented, so that the region having the cushion layer can easily fit into the gluteal fold. On the other hand, the region ahead of the cushion layer can be easily curved by the elastic contractive forces to fit on the crotch.

Preferably, the absorbent article further comprises: a pair of leakage preventing portions extending in a longitudinal direction of the absorbent article and positioned at transversely opposite sides of a region having the cushion layer; and flap portions outside the respective leakage preventing portions, wherein a distance between transversely opposed portions of the compressed groove are decreased so that when the flap portions are folded back against a liquid-receiving side of the absorbent article at fold lines provided outside the respective leakage preventing portions, the flap portions do not overlap with the raised region. With such construction, the absorbent layer can be made thin in the state where the flap portions are thus folded. Therefore, even after the absorbent article is further folded for portable use, the entirety can be made thin.

BRIEF DESCRIPTION OF THE DRAWINGS

The present invention will be understood more fully from the detailed description given hereinafter and from the accompanying drawings of the preferred embodiment of the present invention, which, however, should not be taken to be limitative to the invention, but are for explanation and understanding only.

In the drawings.

DESCRIPTION OF THE PREFERRED EMBODIMENT

The present invention will be discussed hereinafter in detail in terms of the preferred embodiment according to the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structures are not shown in detail in order to avoid unnecessary obscurity of the present invention.

Figure 1:
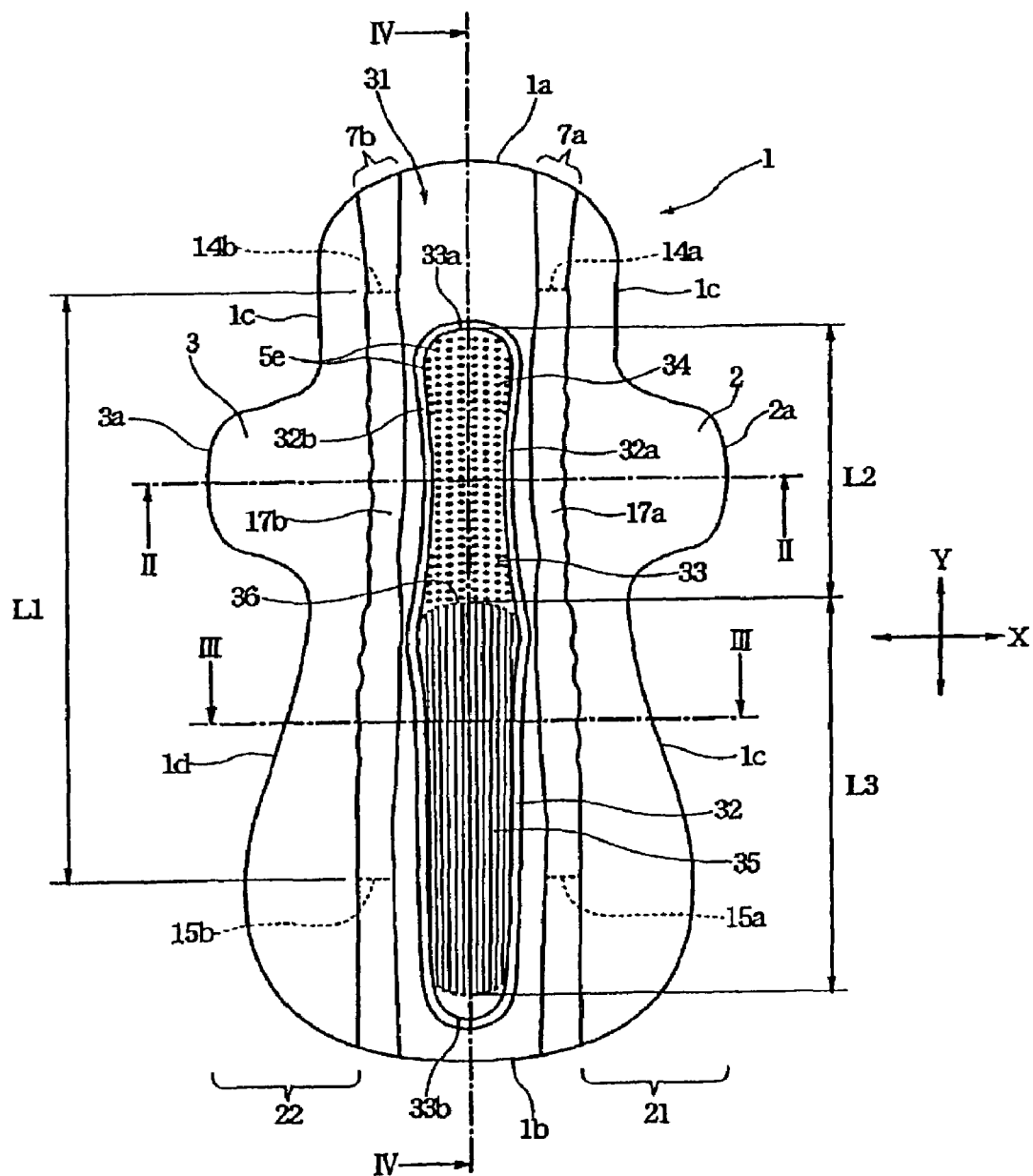
FIG. 1 is a top plan view showing a sanitary napkin as an absorbent article according to one embodiment of the present invention.
Figure 2:
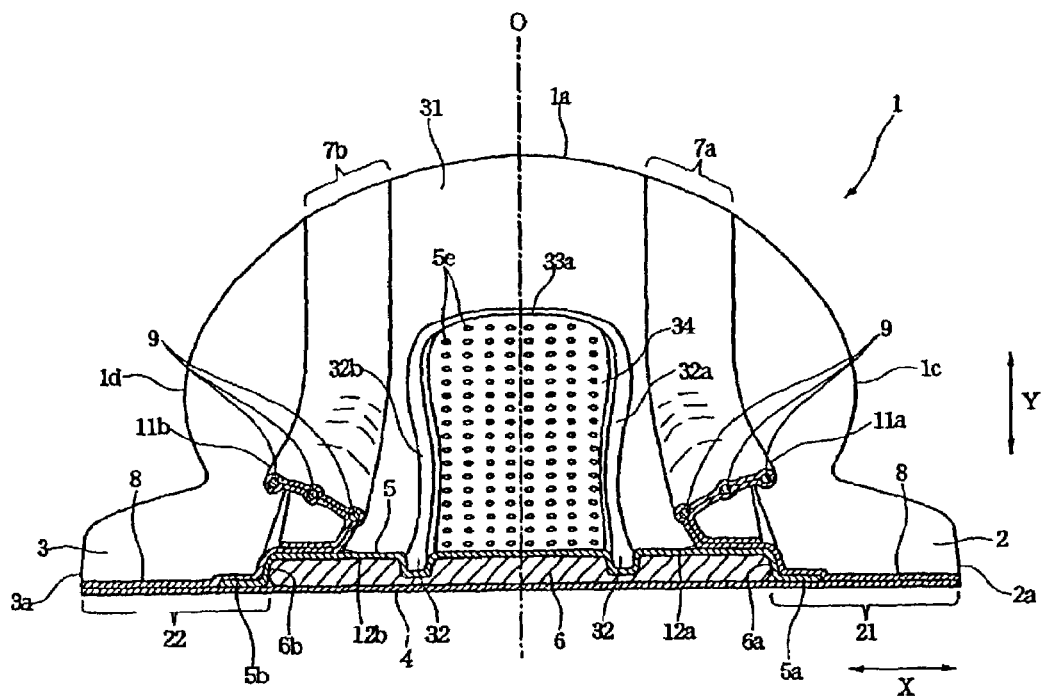
FIG. 2 is a cross sectional view taken along line II-II of FIG. 1.
Figure 3:
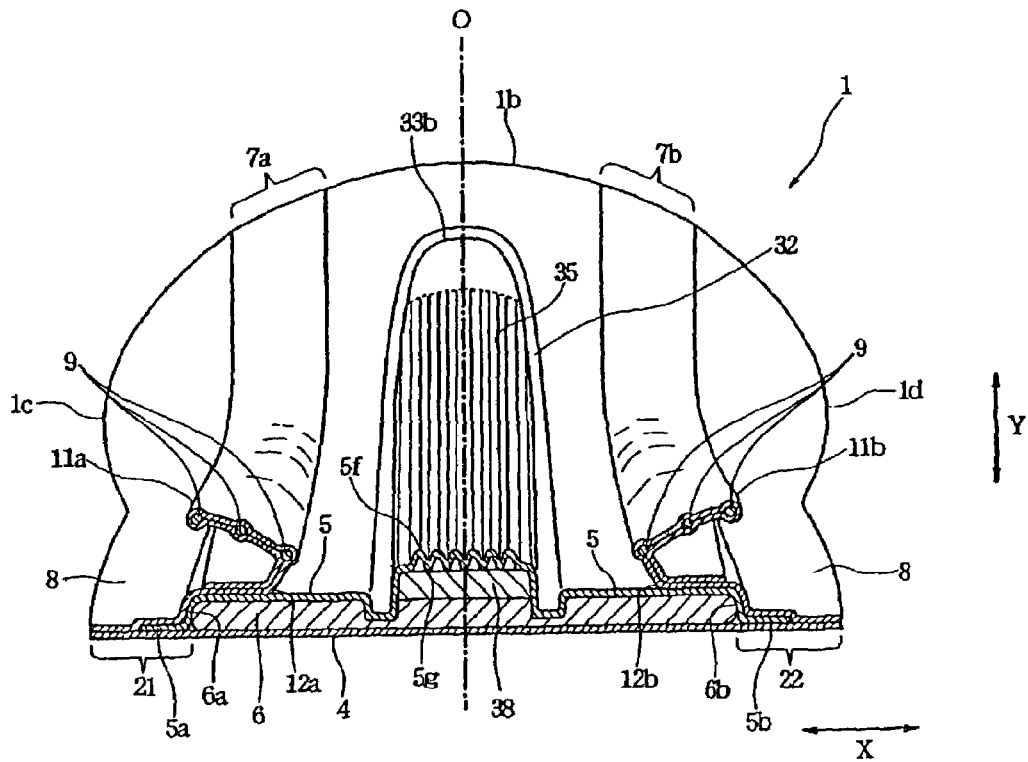
FIG. 3 is another cross sectional view taken along line III-III of FIG. 1.
Figure 4:
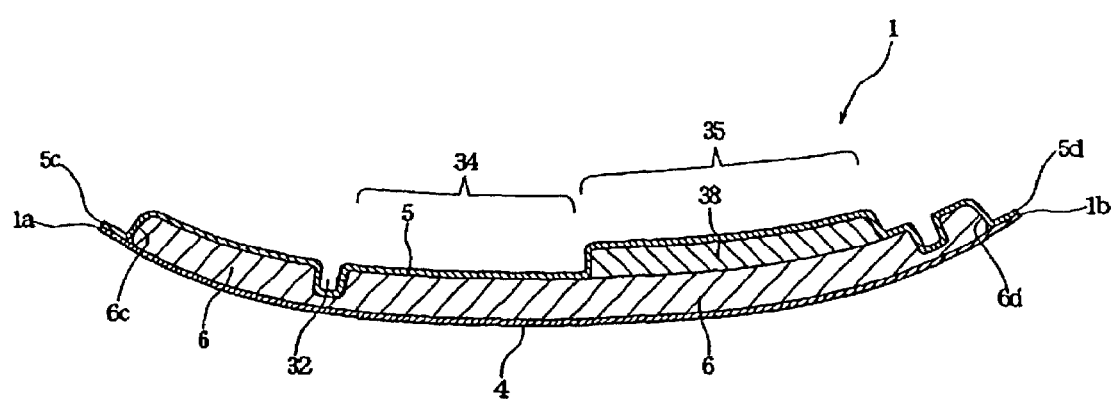
FIG. 4 is a longitudinal sectional view taken along line IV-IV of FIG. 1.
Figure 5:
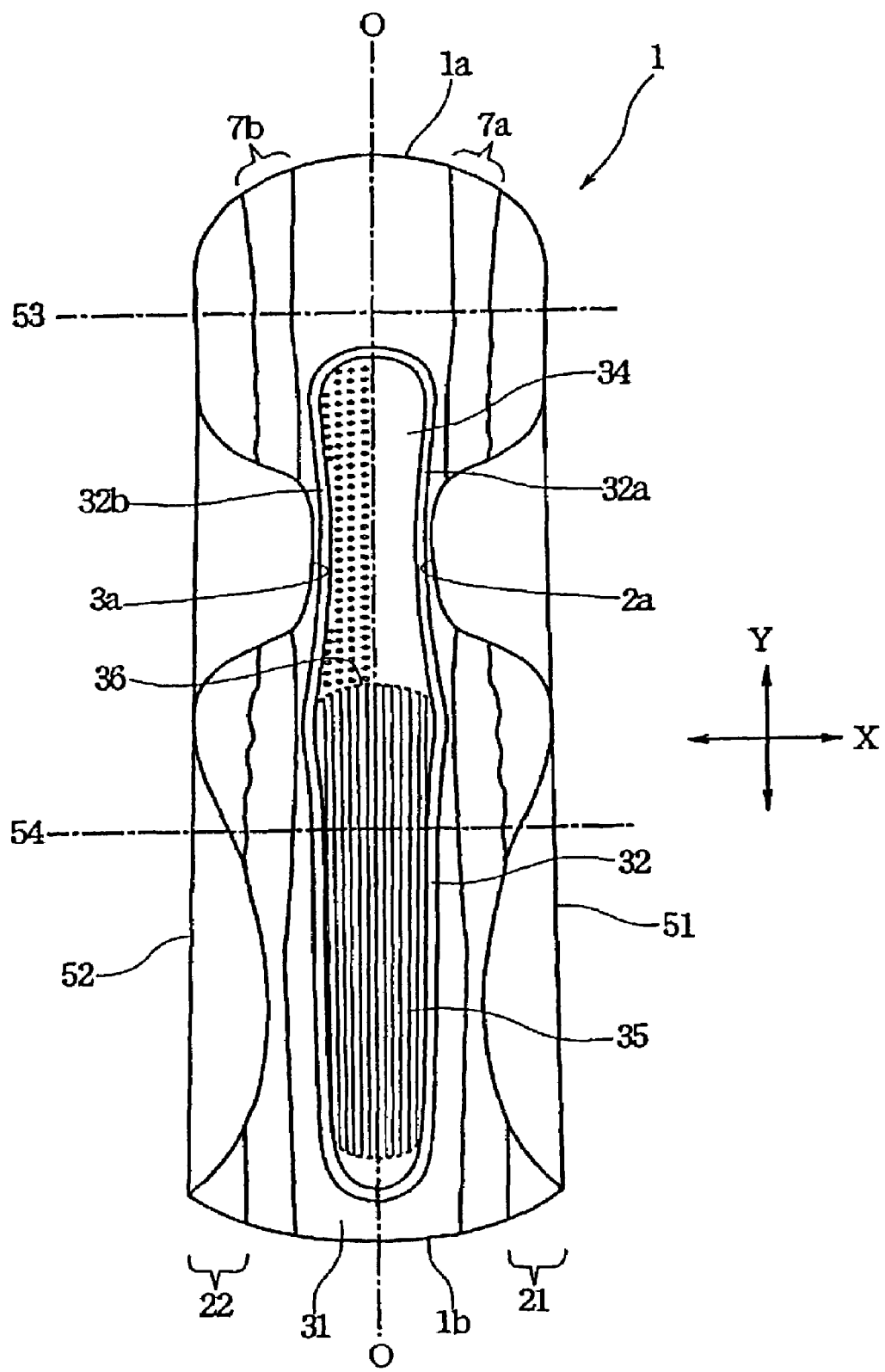
FIG. 5 is a top plan view showing a state where flap portions of the sanitary napkin are folded.

FIG. 1 is a top plan view showing a sanitary napkin 1 as an absorbent article according to one embodiment of the present invention; FIG. 2 is a cross sectional view of the sanitary napkin 1 taken along line II-II of FIG. 1; FIG. 3 is another cross sectional view of the sanitary napkin 1 taken along line III-III of FIG. 1; and FIG. 4 is a longitudinal sectional view of the sanitary napkin 1 taken along line IV-IV (longitudinally extending centerline O-O) of FIG. 1. FIG. 5 is a top plan view showing a state where transversely (laterally) opposed flap portions are folded back against a liquid-receiving side of the sanitary napkin 1.

The sanitary napkin 1 shown in FIGS. 1 to 5 is to be worn by a female during menstruation while being attached to an inner side of a crotch portion of an undergarment.

As seen from the top plan view of FIG. 1, the sanitary napkin 1 has a generally arcuate front edge 1a and a rear edge 1b which is also arcuate. Right-hand and left-hand side edges 1c and 1d are curved. The distance between the right-hand side edge 1c and the left-hand side edge 1d, i.e., the width (dimension in the X-direction) of the sanitary napkin 1 is larger in a rear portion on the side of the rear edge 1b, which is to be brought into contact mainly with the wearer's buttocks, than in a front portion on the side of the front edge 1a, which is to be brought into contact mainly with the wearer's crotch.

The right-hand side edge 1c and the left-hand side edge 1d are protruded laterally (in the X-direction) outwardly in a position offset toward the front edge 1a from a laterally extending centerline of the sanitary napkin 1, thereby forming wing portions 2 and 3.

As shown in FIGS. 2 to 4, the sanitary napkin 1 comprises a liquid-impermeable backsheet 4 and a liquid-permeable topsheet 5. Between the backsheet 4 and the topsheet 5, there is provided an absorbent storage layer (absorbent core) 6 capable of absorbing a liquid and retaining the absorbed liquid.

When viewed from above, the backsheet 4 has the same shape and size as the sanitary napkin 1. That is, the periphery of the backsheet 4 extends in agreement with the front edge 1a, the rear edge 1b, the right-hand side edge 1c, the left-hand side edge 1d, and the edges of the wing portions 2 and 3.

The absorbent storage layer 6 has a right-hand side edge 6a and a left-hand side edge 6b. The right-hand side edge 6a and the left-hand side edge 6b are in substantially parallel relationship with each other and extend substantially linearly in the longitudinal direction of the sanitary napkin 1. As shown in FIG. 4, on the other hand, the front edge 6c of the absorbent storage layer 6 is spaced slightly inwardly apart from the front edge 1a of the sanitary napkin 1, and the rear edge 6d of the absorbent storage layer 6 is spaced slightly inwardly apart from the rear edge 1b of the sanitary napkin 1.

As shown in FIGS. 2 and 3, the topsheet 5 covers the surface of the absorbent storage layer 6. Outside the right-hand and left-hand side edges 6a and 6b of the absorbent storage layer 6, the right-hand and left-hand side edges 5a and 5b of the topsheet 5 are bonded to the surface of the backsheet 4 through a hot-melt adhesive. As shown in FIG. 4, the front edge 5c of the topsheet 5 reaches the front edge 1a of the sanitary napkin 1, so that the topsheet 5 is bonded to the backsheet 4 through the hot-melt adhesive ahead of the front edge 6c of the absorbent storage layer 6. On the other hand, the rear edge 5d of the topsheet 5 reaches the rear edge 1b of the sanitary napkin 1, so that the topsheet 5 is bonded to the backsheet 4 through the hot-melt adhesive behind the rear edge 6d of the absorbent storage layer 6.

At transversely opposite positions spaced apart from the longitudinally extending centerline O-O by a predetermined distance, there are provided leakage preventing portions 7a and 7b. The leakage preventing portions 7a and 7b are positioned above the absorbent storage layer 6. The leakage preventing portions 7a and 7b are formed of a right-hand nonhydrophilic sheet 8 and a left-hand nonhydrophilic sheet 8, respectively. In the leakage preventing portions 7a and 7b, the nonhydrophilic sheets 8 and 8 are folded in two at their tops 11a and 11b. The nonhydrophilic sheets 8 and 8 thus folded are bonded onto the topsheet 5 through a hot-melt adhesive at the root ends 12a and 12b of the respective leakage preventing portions 7a and 7b.

In the respective leakage preventing portion 7a and 7b, a plurality of longitudinally extending elastic members 9 are provided inside the folded nonhydrophilic sheet 8. These elastic members 9 are bonded to the nonhydrophilic sheet 8 while being stretched in the longitudinal direction. From the front ends 14a and 14b (see FIG. 1) to the front edge 1a of the sanitary napkin 1, the respective nonhydrophilic sheet 8 is further folded upon itself and bonded onto the topsheet 5 as a whole. Likewise, from the rear ends 15a and 15b (see FIG. 1) to the rear edge 1b of the sanitary napkin 1, the respective nonhydrophilic sheet 8 is further folded upon itself and bonded onto the topsheet 5 as a whole.

Thus, in a range of length L1 between the front ends 14a and 14b and the rear ends 15a and 15b, the tops 11a and 11b of the leakage preventing portions 7a and 7b are in a free state, to thereby form rising portions 17a and 17b. Elastic contractive forces due to the elastic members 9 act on the rising portions 17a and 17b. More specifically, the elastic contractive forces act on the front ends 14a and 14b and the rear ends 15a and 15b so that the sanitary napkin 1 can be curved in the range of length L1. When the sanitary napkin 1 is curved in the range of length L1, the tops 11a and 11b of the rising portions 17a and 17b are spaced away from the surface of the sanitary napkin 1, so that the leakage preventing portions 7a and 7b is three-dimensionally raised taking the root ends 12a and 12b as starting points.

As shown in FIG. 2, the right-hand nonhydrophilic sheet 8 is outwardly extended from the root end 12a of the leakage preventing portion 7a to the right-hand side edge 1c of the sanitary napkin 1 and the edge 2a of the wing portion 2. The left-hand nonhydrophilic sheet 8 is also outwardly extended from the root end 12b of the leakage preventing portion 7b to the left-hand side edge 1d of the sanitary napkin 1 and the edge 3a of the wing portion 3. Then, the backsheet 4 and the right-hand nonhydrophilic sheet 8 are bonded to each other through a hot-melt adhesive outside the right-hand side edge 5a of the topsheet 5. Likewise, the backsheet 4 and the left-hand nonhydrophilic sheet 8 are bonded to each other through a hot-melt adhesive outside the left-hand side edge 5b of the topsheet 5.

Here, the region outside the right-hand side edge 6a of the absorbent storage layer 6 is designated a flap portion 21, in which the backsheet 4 and the right-hand nonhydrophilic sheet 8 are mainly bonded to each other. The wing portion 2 is part of the flap portion 21. On the other hand, the region outside the left-hand side edge 6b of the absorbent storage layer 6 is designated a flap portion 22, in which the backsheet 4 and the left-hand nonhydrophilic sheet 8 are mainly bonded to each other. The wing portion 3 is part of the flap portion 22.

The region between the leakage preventing portions 7a and 7b is designated liquid-receiving region 31. In this liquid-receiving region 31, a compressed groove 32 is formed by heating the absorbent storage layer 6 and the topsheet 5 under pressure to be recessed. The compressed groove 32 extends to surround a central region of the liquid-receiving region 31. The region surrounded by the compressed groove 32 is designated raised region 33. The raised region 33 is elongated in the longitudinal direction of the sanitary napkin 1, so that the front end 33a of the raised region 33 is positioned behind the front ends 14a, 14b of the rising portions 17a, 17b of the leakage preventing portions 7a, 7b and the rear end 33b of the raised region 33 is positioned behind the rear ends 15a, 15b of the rising portions 17a, 17b.

The front region of the raised region 33 having a length L2 is designated front absorbent region 34, and the rear region of the raised region 33 having a length L3 is designated rear cushion region 35. The boundary 36 between the front absorbent region 34 and the rear cushion region 35 is not spaced more than 20 mm apart from the transversely extending centerline of the sanitary napkin 1.

In the front absorbent region 34, the surface of the absorbent storage layer 6 is covered with the liquid-permeable topsheet 5. The front absorbent region 34 is to be brought into contact mainly with the private part of a wearer. As shown in FIGS. 3 and 4, in the rear cushion region 35, a cushion layer 38 is disposed between the absorbent storage layer 6 and the topsheet 5. The cushion layer 38 is formed of a material more flexible than the absorbent storage layer 6.

The topsheet 5 has a large number of liquid passages (through-holes) 5e at least in a portion covering the front absorbent region 34 so that a menstrual blood discharged from the private part of a female can be absorbed by the absorbent storage layer 6 through the topsheet 5. In the rear cushion region 35, on the other hand, the topsheet 5 is shaped to have a corrugated cross-sectional shape, of which hills 5f and valleys 5g are regularly alternated in the transverse direction (X-direction) and continuously extended in the longitudinal direction (Y-direction), as shown in FIG. 3.

In the rear cushion region 35, since the topsheet 5 is corrugated to be extensible at least in the transverse direction (X-direction), the cushion layer 38 can deform flexibly. As a result, the rear cushion region 35 can deform flexibly and fit into the gluteal fold of a wearer. Accordingly, when the wearer is asleep, for example, a menstrual blood flowing down the gluteal fold can be dammed up by the rear cushion region 35, and such menstrual blood having reached the rear cushion region 35 passes through the corrugated topsheet 5, introduced into the absorbent storage layer 6 through the cushion layer 38, and absorbed by the absorbent storage layer 6. Thus, the menstrual blood flowing down the gluteal fold can be prevented from leaking rearwardly out of the rear edge 1b of the sanitary napkin 1.

Next, the properties of the rear cushion region 35 and the portions related thereto will be described.

First, when a tensile force of 490 mN is applied in the transverse direction (X-direction) to a portion of the topsheet 5 covering the rear cushion region 35 and having a width of 25 mm in the longitudinal direction (Y-direction), the extension (elongation) is at least 30%. The extension is expressed by $(L1-L0)/L0 \times 100$ (%), wherein L0 represents a given length (e.g., 50 mm) in the transverse direction before the tensile force is applied to the topsheet 5 and L1 represents a length in the transverse direction when the tensile force is applied to the topsheet 5.

If the extension is less than 30%, the cushion layer 38 is held down by the topsheet 5 to increase the density of the cushion layer 38, so that the rear cushion region 35 hardly deforms in conformity to the shape of the gluteal fold. Here, although there is no special reason to establish the upper limit of the extension, the upper limit of the extension will be about 150%.

On the other hand, when the portion of the topsheet 5 covering the rear cushion region 35 is extended in the transverse direction, the tensile breaking strength is preferably at least 980.7 mN per 25 mm width. If the tensile breaking strength is much less than 980.7 mN, when a deformation force is applied to the rear cushion region 35, a crack or the like is liable to occur in the topsheet 5.

The measurements of the extension and the tensile breaking strength may be carried out using "AUTOGRAPH AGS-1 kNG" manufactured by SHIMADZU, Japan. Here, a sheet having the same construction as the portion of the topsheet 5 covering the rear cushion region 35 is cut out into a test sample having a width of 25 mm in a direction along which the hills and valleys are extended (corresponding to the longitudinal direction of the sanitary napkin 1) and a length of 100 mm in a direction along which the hills and valleys are alternated (corresponding to the transverse direction of the sanitary napkin 1). The extension and the tensile breaking strength can be obtained by extending such test sample in the direction along which the hills and valleys are alternated, at a tensile rate of 100 mm/minute with a chuck-to-chuck distance of 50 mm.

With the extension of the topsheet 5 in the transverse direction being equal to or more than 30% in the rear cushion region 35, the following compression properties can be provided to the rear cushion region 35.

Throughout the disclosure, the properties of the rear cushion region 35 of the sanitary napkin 1 and the compression properties of the cushion layer 38 alone are expressed by values determined by using Automatic Compression Tester "KES FB3-A" manufactured by Kato Tech, Japan.

Figure 6:
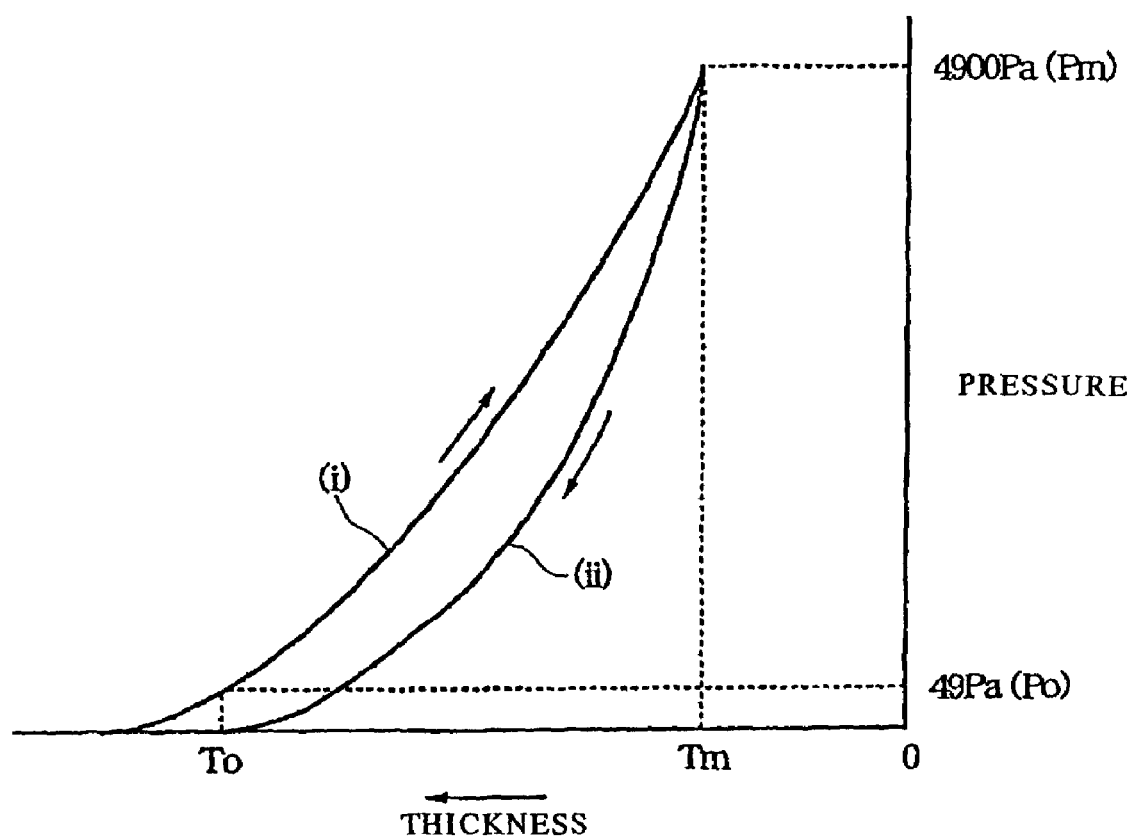
FIG. 6 is a diagram showing compression properties.

For measurement of such values, the sanitary napkin 1 or the cushion layer 38 alone is put on the Automatic Compression Tester as a test sample, and then, the sample is pressed with the circular pressure plate having an area of 2 cm$^2$. In the diagram of FIG. 6, the applied pressure is plotted in ordinate, and the thickness of the test sample is plotted in abscissa. The thickness of the pressed region of the test sample, when an initial pressure of P0=49 Pa (0.5 g/cm$^2$) is applied to the test sample with the pressure plate, is designated initial thickness T0. Then, the compression pressure is increased linearly at a compression rate of 0.1 cm/second from the initial pressure P0 to the maximum compression pressure of Pm=4,900 Pa (50 g/cm$^2$). Tm represents the thickness of the pressed region of the test sample when the maximum compression pressure Pm is applied thereto.

The compression energy WC per 1 cm$^2$ of the test sample is expressed by a value of the definite integral along the curve (i) of FIG. 6 between Tm and T0, i.e., WC=∫P·dT (P indicates pressure; T indicates thickness). The compressive hardness (LC value) is obtained according to LC=2WC/{(T0-Tm)Pm} (dimensionless).

On the other hand, the compressive recovery (RC value) is obtained according to RC=R/WC×100 (%), wherein R is a value of the definite integral along the recovery curve (ii) between Tm and T0, i.e., R=∫P·dT.

In the sanitary napkin 1, the initial thickness T0 of the rear cushion region 35 is at least 10 mm. If the initial thickness T0 is less than 10 mm, when the sanitary napkin 1 is worn by a wearer by attaching the exterior surface of the backsheet 4 to the inner side of a crotch portion of an undergarment through a pressure-sensitive adhesive, the rear cushion region 35 hardly fits into the gluteal fold. It is preferred that a difference between T0 and Tm is at least 3 mm. With the difference between T0 and Tm being at least 3 mm, even if the pressure acting on the rear cushion region 35 from the wearer's body varies during wear, the rear cushion region 35 can be kept fitting into the gluteal fold. Accordingly, it is also preferred that the thickness Tm upon compression is at most 7 mm.

On the other hand, the compressive hardness (LC value) of the rear cushion region 35 is in a range of 0.5 to 0.65. Here, the LC value refers to a degree of linearity of the change in thickness versus the change in pressure. For example, if the line of FIG. 6 showing the changes in thickness and pressure is not curved but a straight line of a linear function, the LC value is 1. If the LC value is less than 0.5, the change in thickness versus the change in pressure is much, so that when a pressure from the wearer's body acts on the rear cushion region 35, the cushion layer 38 is easily deformed to cause the rear cushion region 35 to lose shape. If the LC value is more than 0.65, on the other hand, the change in thickness versus the change in pressure is little, so that the wearer feels it hardish. In addition, when a pressure from the wearer's body changes, the rear cushion region 35 hardly fits into the gluteal fold.

On the other hand, the compressive recovery (RC value) of the rear cushion region 35 refers to a ratio of the energy at the time of recovery indicated at (ii) to the energy of the compression curve indicated at (i) in FIG. 6. The RC value is at least 35%. In this case, the upper limit is 100%. With the compressive recovery being at least 35%, even when the pressure acting on the rear cushion region 35 from the wearer's body is decreased during wear of the sanitary napkin 1, the rear cushion region 35 can be well recovered. Therefore, the rear cushion region 35 can constantly fit into the gluteal fold regardless of the change of the pressure from the wearer's body. More preferably, the compressive recovery is at least 50%.

In case where the measurement is carried out for the cushion layer 38 alone, on the other hand, it is preferred that the initial thickness T0' is at least 3 mm, the thickness Tm' upon compression is at least 1.5 mm. It is also preferred that the compressive hardness (LC value) is at least 0.35 and the compressive recovery (RC value) is at least 30%.

If the initial thickness T0', the thickness Tm' upon compression, the LC value, and the RC value of the cushion layer 38 are set within the above-mentioned ranges, the initial thickness T0, the thickness Tm upon compression, the LC value, and the RC value of the rear cushion region 35 can be readily set within the above-mentioned ranges even if the absorbent storage layer 6 is formed of commonly used absorbent materials.

On the other hand, the Gurley stiffness at the region having the compressed groove 32 is larger than the Gurley stiffness at the rear cushion region 35. It is preferred that the Gurley stiffness at the region having the compressed groove 32 is 4.9 to 34.3 mN, and the Gurley stiffness at the rear cushion region 35 is 1.96 to 14.7 mN.

For measurement of the Gurley stiffness, a compressed sheet laminate having the same construction as the compressed groove 32 and a sheet laminate having the same construction as the rear cushion region 35 of the sanitary napkin are prepared, and then cut into test samples having a size of 51 mm (in a direction corresponding to the longitudinal direction of the sanitary napkin)×12.7 mm (in a direction corresponding to the transverse direction of the sanitary napkin). The stiffness (mN) can be measured such that the longitudinal end of the test sample is held in a chuck of a Gurley Stiffness Tester (manufactured by YASUDA SEIKI, Japan), and then, the reading is taken on a pendulum as the chuck is swung at a constant speed. This Gurley Stiffness Test is carried out based on JIS-L1018.

If the Gurley stiffness of the compressed groove 32 is less than the above-mentioned range, the compressed groove 32 cannot serve the function of maintaining the shape of the raised region 33, so that the raised region 33 is liable to twist during wear. If the Gurley stiffness of the compressed groove 32 is more than the above-mentioned range, on the other hand, the stiffness of the entire sanitary napkin 1 is excessively increased to give a stiff feel to the wearer. If the Gurley stiffness of the rear cushion region 35 is less than the above-mentioned range, the raised region 33 surrounded by the compressed groove 32 is crushed during formation of the compressed groove 32. Therefore, it is difficult to maintain the shape of the raised region 33. If the Gurley stiffness of the rear cushion region 35 is more than the above-mentioned range, on the other hand, the rear cushion region is excessively stiff to impair a feel upon wearing.

As shown in FIG. 1, the front ends 14a, 14b of the rising portion 17a, 17b of the leakage preventing portions 7a, 7b are positioned ahead of the front absorbent region 34 as well as the front end (boundary 36) of the rear cushion region 35. On the other hand, the rear ends 15a, 15b of the rising portion 17a, 17b are positioned ahead of the rear end of the rear cushion region 35 and behind the boundary 36.

The elastic contractive forces of the elastic members 9 given to the rising portion 17a, 17b function to bend the sanitary napkin 1 between the front ends 14a, 14b and the rear ends 15a, 15b. However, since the rear ends 15a, 15b are positioned ahead of the rear end of the rear cushion region 35, large bending force does not act on the rear cushion region 35 but mainly acts on the front absorbent region 34. Therefore, the front absorbent region 34 is curved in conformity to the crotch of a wearer to readily fit on the wearer's private part. On the other hand, the rear cushion region 35 conforms to the buttocks of a wearer without being curved much, so that the rear cushion region 35 can readily fit into the gluteal fold.

The sanitary napkin 1 thus constructed is folded and wrapped in a packaging sheet (not shown). Firstly, as shown in FIG. 5, the rear portion and the wing portion 2 of the flap portion 21 are folded back against the liquid-receiving side of the sanitary napkin 1 at a longitudinally extending fold line 51 provided outside the leakage preventing portion 7a; and the rear portion and the wing portion 3 of the flap portion 22 are folded back against the liquid-receiving side of the sanitary napkin 1 at a longitudinally extending fold line 52 provided outside the leakage preventing portion 7b. The sanitary napkin 1 folded into the state of FIG. 5 is further folded at transversely extending fold lines 53 and 54. Thereafter, the sanitary napkin 1 is wrapped in a packaging sheet.

Here, as shown in FIG. 5, the flap portion 21 and 22 folded at the longitudinally extending fold lines 51 and 52 do not overlap with the raised region 33. It should be noted at this point that transversely opposed portions 32a and 32b of the compressed groove 32 defining the side edges of the front absorbent region 34 of the raised region 33 are curved toward the centerline O-O so that the edges 2a and 3a of the wing portions 2 and 3 folded back against the liquid-receiving side of the sanitary napkin 1 face the curved portions 32a and 32b, thereby preventing the wing portions 2 and 3 from overlapping with the raised region 33.

Therefore, the thickness of the sanitary napkin 1 folded into the state of FIG. 5 is minimized, so that when the sanitary napkin 1 is further folded at the transversely extending fold lines 53 and 54, the entirety can be made thin. Accordingly, the package of the sanitary napkin 1 wrapped in a packaging sheet can be made thin and compact.

Next, preferred materials for forming the sanitary napkin will be described.

The topsheet 5 may be formed of a nonwoven fabric, a nonwoven fabric having the liquid passages (through-holes) 5e distributed at least in a portion for covering the front absorbent region 34, or a polyethylene film having such liquid passages distributed over the entirety. In the embodiment shown, the portion of the topsheet 5 covering the rear cushion region 35 is corrugated to have the hills 5f and valleys 5g extending in the longitudinal direction (Y-direction). For forming such corrugation, two rolls having a large number of projecting ribs and recesses on their circumferential surfaces are mated to fit the protrusions into the recesses, and the topsheet is supplied in between the two rolls while heating the roll surfaces to 110 to 120° C. With such process, the topsheet 5 can be shaped to have the corrugation. With the corrugation, the topsheet 5 is allowed to elastically extend in the transverse direction.

To give a concrete example, the topsheet 5 is formed of a through-air bonded nonwoven fabric having a basis weight of 25 g/m$^2$, which is comprised of sheath/core bicomponent synthetic fibers having a fineness of 2.2 dtex and fusion-bonded to each other with heated air, of which the sheath is PE (polyethylene) and the core is PET (polyethylene terephthalate). This through-air bonded nonwoven fabric is supplied in between the two rolls to have the corrugation in the portion for covering the rear cushion region 35, wherein the height from the bottom of the recess to the top of the protrusion of the rolls is set at 1.0 mm, the pitch of the protrusions and the recesses of the rolls is set at 1.8 mm, the clearance between the opposed two rolls in the radial direction is set at 0.2 mm, and the roll surfaces are heated to 110 to 120° C.

In an alternative, a stretch spunbonded nonwoven fabric which is elastically extensible in the transverse direction, or an elastomeric resin sheet formed with liquid passages may be used for the topsheet 5. In case where the topsheet 5 is satisfactorily extensible even without forming the corrugation, it is not required to shape it to have such corrugation. Even in such case, however, it is also possible to form the corrugation so as to increase the extension (%) of the topsheet utilizing both the nature of the sheet and the corrugation.

The cushion layer 38 is made of a thermoplastic resin to have three-dimensionally elastically deformable framework, as exemplified by a through-air bonded nonwoven fabric, or a foamed resin sheet having interconnected cells passing through it from top to bottom. It should be noted that the cushion layer 38 is treated to be hydrophilic.

In case where the cushion layer 38 is formed of a through-air bonded nonwoven fabric, constituent fibers are thermoplastic and preferably made of at least two kinds of synthetic resin shaving different melting points. For example, they are sheath/core, side-by-side, or hollow bicomponent fibers of polyolefin resin and polyester resin. In order to set the compression properties of the cushion layer 38 within the above-mentioned ranges, it is preferred that the fiber thickness is 10 to 50 μm and the number of crimp per 25 mm length is 10 to 35. Here, the fibers are treated to be hydrophilic by coating the surface of the fibers with a hydrophilic agent or mixing the fibers with a hydrophilic agent.

In order to set the compression properties of the cushion layer 38 within the above-mentioned ranges by using such through-air bonded nonwoven fabric or the like, the through-air bonded nonwoven fabric or the like should be bulky and of low fiber density. However, in the process of continuously manufacturing the sanitary napkins 1, the through-air bonded nonwoven fabric or the like is first installed in the form of material roll, and then unwound from the material roll for processing. Therefore, the sheet material is compressed due to the pressure for winding it into the form of material roll. If the compressed sheet material is used as it is, it is impossible to obtain the foregoing compression properties.

Accordingly, in the manufacturing process of the sanitary napkin, it is preferred that the thermoplastic sheet materials unwound from the material roll for forming the cushion layer is first brought into contact with a heated roll or applied heated air to restore its bulkiness, supplied on the absorbent storage layer 6, and then covered with the topsheet 5.

For the cushion layer 38, preferably used is a through-air bonded nonwoven fabric having a basis weight of 20 g/m$^2$, which is comprised of sheath/core bicomponent synthetic fibers having a fineness of 4.4 dtex, of which the sheath is PE and the core is PET. The through-air bonded nonwoven fabric, after unwound from the material roll, is brought into contact with the surface of a heated roll having a surface temperature of 100 to 130° C. to restore its bulkiness. Here, the basis weight of the cushion layer 38 is preferably 40 to 200 g/m$^2$. Therefore, two or more through-air bonded nonwoven fabrics having such basis weight are preferably stacked. Alternatively, the through-air bonded nonwoven fabric having such basis weight is preferably folded in two or more.

The backsheet 4 is liquid-impermeable, as exemplified by a resin film made of PE (polyethylene), PP (polypropylene), PET (polyethylene terephthalate), EVA (ethylene-vinyl acetate copolymer), or a combination of two or more thereof. The resin film may be finely apertured to provide moisture permeability by adding filler or the like and then elongating it. In an alternative, a laminate of resin and paper, a laminate of nonwoven fabric and resin film or the like may be employed.

For the absorbent storage layer 6, a mixture of crushed pulp and SAP (superabsorbent polymer) wrapped in a liquid-permeable paper or cellulose sheet, cellulose fibers processed with a binder into a sheet form, fluff pulp, air-laid pulp, open-cell type hydrophilic foam, thin paper, spunlaced nonwoven fabric comprising hydrophilic fibers, meltblown nonwoven fabric treated to be hydrophilic, absorbent paper, cotton linter pulp, or combinations thereof may be employed. However, any other materials may be employed as long as suitable for use as the absorbent layer.

The nonhydrophilic sheet 8 is preferably formed of a material which is flexible and through which a liquid never permeates or passes. For example, the nonhydrophilic sheet 8 is formed of a nonwoven fabric comprised of PP fibers or bicomponent fibers of PE/PP, PE/PET, PP/EVA or the like having a fineness of 1.1 to 6.7 dtex. The nonwoven fabric is preferably a nonwoven fabric manufactured by through-air bonding method. Alternatively, a spunbonded nonwoven fabric manufactured by continuously spinning fibers may be employed in place of the through-air bonded nonwoven fabric. It is also possible to employ a sheet formed by laminating PE resin to such through-air bonded or spunbonded nonwoven fabric.

In the foregoing embodiment, the cushion layer 38 is provided in the rear region of the sanitary napkin 1 so that the rear cushion region 35 can fit into the gluteal fold. However, it is also possible to provide the cushion layer in the center region of the sanitary napkin so that the cushion region can fit on the private part.

EXAMPLES

Examples

Sanitary napkins of Examples 1 to 3 having the same construction as that of the sanitary napkin shown in FIG. 1 were prepared by selecting preferred components from Tables 1 to 4. Table 1 shows the constructions and properties of three kinds of components A, B, C for the topsheet; Table 2 shows the constructions and properties of four kinds of components D, E, F, G for the cushion layer; and Table 3 shows the constructions and properties of three kinds of components H, I, J for the absorbent storage layer. Table 4 shows the constructions and properties of the sanitary napkins of Examples 1 to 4.

TABLE 1

| | Construction | Basis weight (g/m$^2$) | Corrugation | Extension (%) | Tensile Breaking Strength (mN/25 mm) |
|---|---|---|---|---|---|
| A | PE/PET through-air bonded nonwoven | 25 | Not formed | 22 | 2851 |
| B | PE/PET through-air bonded nonwoven | 25 | Formed | 48 | 2156 |
| C | Stretch spunbonded nonwoven | 25 | Not formed | 130 | 5380 |

TABLE 2

| | Construction | Basis weight (g/m²) | Density (g/cm³) | Initial thickness (T0) (mm) | Thickness upon compression (Tm) (mm) | Compressive hardness (LC) | Compressive recovery (RC) (%) |
|---|---|---|---|---|---|---|---|
| D | PE/PP through-air bonded nonwoven | 60 | 0.024 | 2.52 | 0.62 | 0.28 | 37 |
| E | PE/PP through-air bonded nonwoven | 60 | 0.018 | 3.25 | 0.82 | 0.44 | 37 |
| F | PE/PP through-air bonded nonwoven | 80 | 0.017 | 4.64 | 1.22 | 0.43 | 46 |
| G | PE/PP through-air bonded nonwoven | 60 | 0.010 | 5.86 | 1.07 | 0.47 | 50 |

TABLE 3

| | Construction | Basis weight (g/m²) | Thickness (mm) | Density (g/cm³) |
|---|---|---|---|---|
| H | Pulp/SAP | 200 | 2.5 | 0.08 |
| I | Pulp/SAP | 600 | 7.5 | 0.08 |
| J | Pulp/SAP | 800 | 10 | 0.08 |

TABLE 4

| | | Ex. 1 | Ex. 2 | Ex. 3 | Ex. 4 |
|---|---|---|---|---|---|
| Construction of Examples | Topsheet | B | B | B | C |
| | Cushion layer | E | F | G | G |
| | Absorbent layer | I | I | I | I |
| Properties of Examples | Initial thickness (T0) (mm) | 11.3 | 12 | 15.7 | 15.4 |
| | Thickness upon compression (Tm) (mm) | 6.9 | 6.4 | 9.6 | 9.3 |
| | Compressive hardness (LC) | 0.57 | 0.56 | 0.59 | 0.57 |
| | Compressive recovery (RC) (%) | 42.2 | 44 | 42.4 | 41 |

Comparative Examples

The components shown in Tables 1 to 3 were combined as shown in Table 5 to prepare sanitary napkins of Comparative Examples 1 to 3. Table 5 shows the constructions and properties of the sanitary napkins of Comparative Examples 1 to 3.

TABLE 5

| | | Com. Ex.1 | Com. Ex.2 | Com. Ex.3 |
|---|---|---|---|---|
| Construction of Comparative Examples | Topsheet | A | B | A |
| | Cushion layer | Not provided | D | G |
| | Absorbent layer | J | H | I |
| Properties of Comparative Examples | Initial thickness (T0) (mm) | 12.6 | 5.2 | 12.3 |
| | Thickness upon compression (Tm) (mm) | 9.6 | 2.8 | 7.9 |
| | Compressive hardness (LC) | 0.624 | 0.412 | 0.7 |
| | Compressive recovery (RC) (%) | 29.2 | 4 | 33 |

Evaluation

The sanitary napkins of Examples and Comparative Examples were worn and evaluated with respect to fit and foreign body sensation by twenty female monitors. Regarding the fit, whether or not the surface of the sanitary napkin was certainly in close contact with the area from the vaginal opening to the gluteal fold, was evaluated. Regarding the foreign body sensation, whether or not an unpleasantness was given during wear of the sanitary napkin, was evaluated.

The sanitary napkins were evaluated with respect to the fit and foreign body sensation by letting the monitors assign marks according to the following criterion. Table 6 shows the evaluation results which are averages of such marks.

(Criterion)
  5: Very good
  4: Not bad
  3: Neither good nor bad
  2: Not very good
  1: Bad

TABLE 6

| | | Ex. 1 | Ex. 2 | Ex. 3 | Ex. 4 | Com. Ex. 1 | Com. Ex. 2 | Com. Ex. 3 |
|---|---|---|---|---|---|---|---|---|
| Evaluation results | Fit | 4.1 | 4.3 | 4.5 | 4.4 | 3.7 | 2.4 | 3.3 |
| | Foreign body sensation | 3.9 | 3.8 | 4.3 | 4.1 | 2.5 | 4.2 | 3.8 |

As understood from the above results, the sanitary napkins of Examples were superior in both fit and foreign body sensation to those of Comparative Examples, since the difference between the initial thickness T0 and the thickness Tm upon compression was at least 3 mm, the LC value was in the range of 0.5 to 0.65, and the RC value was at least 35%.

As has been described above, in the present invention, the region having the cushion layer can flexibly deform to fit in conformity to the unevenness of the wearer's body.

Although the present invention has been illustrated and described with respect to exemplary embodiment thereof, it should be understood by those skilled in the art that the foregoing and various other changes, omission and additions may be made therein and thereto, without departing from the spirit and scope of the present invention. Therefore, the present invention should not be understood as limited to the specific embodiment set out above but to include all possible embodiments which can be embodied within a scope encompassed and equivalent thereof with respect to the feature set out in the appended claims.

What is claimed is:

1. An absorbent article comprising:
a liquid-permeable topsheet;
a backsheet;
an absorbent storage layer between the topsheet and the backsheet; and
a cushion layer between the topsheet and the absorbent storage layer,
wherein the absorbent storage layer is compressed forming a compressed groove surrounding a raised region, the raised region is elongated in a longitudinal direction of the absorbent article, the cushion layer is confined within a rear region of the raised region, and the topsheet is corrugated within the rear region to have hills and valleys extending in the longitudinal direction and alternating with each other in a transverse direction of the absorbent article,
when a tensile force of 490 mN per 25 mm width is applied to the topsheet in a transverse direction crossing the cushion layer, an extension is at least 30%, and
when the absorbent article is pressed from above in the rear region having the cushion layer with a pressure varying from 49 Pa to 4,900 Pa, an initial thickness T0 of the pressed region of the absorbent article for a pressure of 49 Pa is at least 10 mm, a compressive hardness (LC value) is 0.5 to 0.65, and a compressive recovery (RC value) is at least 35%.

2. The absorbent article as set forth in claim 1, wherein when Tm represents a thickness of the pressed region of the absorbent article for a pressure of 4,900 Pa, a difference between the initial thickness T0 and the thickness Tm is at least 3 mm.

3. The absorbent article as set forth in claim 1, wherein when the cushion layer alone is pressed from above with a pressure varying from 49 Pa to 4,900 Pa, an initial thickness T0' for the pressure of 49 Pa is at least 3 mm, a thickness Tm' for the pressure of 4,900 Pa is at most 1.5 mm, a compressive hardness (LC value) is at least 0.35, and a compressive recovery (RC value) is at least 30%.

4. The absorbent article as set forth in claim 1, wherein a Gurley stiffness at the compressed groove is 4.9 to 34.3 mN, a Gurley stiffness at the rear region is 1.96 to 14.7 mN, and the Gurley stiffness at the compressed groove is larger than the Gurley stiffness at the rear region.

5. The absorbent article as set forth in claim 1, which further comprises:
a pair of leakage preventing portions extending in a longitudinal direction of the absorbent article at transversely opposite sides of the raised region, the leakage preventing portions having elastic members adapted to exhibit an elastic contractive force in the longitudinal direction,
wherein a portion of each leakage preventing portion to be elastically contracted by the elastic member has a front end ahead of a front end of the cushion layer and has a rear end ahead of a rear end of the cushion layer.

6. The absorbent article as set forth in claim 1, which further comprises:
a pair of leakage preventing portions extending in a longitudinal direction at transversely opposite sides of the raised region; and
flap portions outside the respective leakage preventing portions,
wherein transversely opposed portions of the compressed groove are concavely curved to decrease a distance therebetween so that the flap portions do not overlap with the raised portion when the flap portions are folded back against a liquid-receiving side of the absorbent article at fold lines provided outside the respective leakage preventing portions.

7. An absorbent article comprising:
a liquid-permeable topsheet;
a backsheet;
an absorbent storage layer between the topsheet and the backsheet; and
a cushion layer between the topsheet and the absorbent storage layer,
wherein the absorbent storage layer is compressed forming a compressed groove surrounding a raised region, the raised region is elongated in a longitudinal direction of the absorbent article, the cushion layer is confined within a rear region of the raised region, and the topsheet is corrugated within the rear region to have hills and valleys extending in the longitudinal direction and alternating with each other in a transverse direction of the absorbent article.

8. The absorbent article as set forth in claim 7,
wherein when a tensile force of 490 mN per 25 mm width is applied to the topsheet in a transverse direction crossing the cushion layer, an extension is at least 30%, and
when the absorbent article is pressed from above in the rear region having the cushion layer with a pressure varying from 49 Pa to 4,900 Pa, an initial thickness T0 for the pressure of 49 Pa is at least 10 mm, a compressive hardness (LC value) is 0.5 to 0.65, and a compressive recovery (RC value) is at least 35%, and a thickness Tm for the pressure of 4,900 Pa, a difference between the initial thickness T0 and the thickness Tm is at least 3 mm.

9. The absorbent article as set forth in claim 7, wherein when the cushion layer alone is pressed from above with a pressure varying from 49 Pa to 4,900 Pa, an initial thickness T0' for the pressure of 49 Pa is at least 3 mm, a thickness Tm' for the pressure of 4,900 Pa is at most 1.5 mm, a compressive hardness (LC value) is at least 0.35, and a compressive recovery (RC value) is at least 30%.

10. The absorbent article as set forth in claim 7, wherein a Gurley stiffness at the compressed groove is 4.9 to 34.3 mN, a Gurley stiffness at the rear region is 1.96 to 14.7 mN, and the Gurley stiffness at the compressed groove is larger than the Gurley stiffness at the rear region.

11. The absorbent article as set forth in claim 7, which further comprises:
a pair of leakage preventing portions extending in a longitudinal direction at transversely opposite sides of the raised region, the leakage preventing portions having elastic members adapted to exhibit an elastic contractive force in the longitudinal direction,
wherein a portion of each leakage preventing portion to be elastically contracted by the elastic member has a front end ahead of a front end of the cushion layer and has a rear end ahead of a rear end of the cushion layer.

12. The absorbent article as set forth in claim 7, which further comprises:
a pair of leakage preventing portions extending in the longitudinal direction at transversely opposite sides of the raised region; and
flap portions outside the respective leakage preventing portions,
wherein transversely opposed portions of the compressed groove are concavely curved to decrease a distance therebetween so that the flap portions do not overlap with the raised portion when the flap portions are folded back against a liquid-receiving side of the absorbent article at fold lines provided outside the respective leakage preventing portions.

13. The absorbent article as set forth in claim 1, wherein the topsheet and the cushion layer are through-air bonded non-woven fabric.

14. The absorbent article as set forth in claim 7, wherein the topsheet and the cushion layer are through-air bonded non-woven fabric.

* * * * *